(12) United States Patent
Kawakami

(10) Patent No.: US 7,186,511 B2
(45) Date of Patent: Mar. 6, 2007

(54) OXIDASE

(75) Inventor: Masakatsu Kawakami, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 10/509,622

(22) PCT Filed: Jun. 5, 2003

(86) PCT No.: PCT/JP03/07148

§ 371 (c)(1),
(2), (4) Date: Sep. 29, 2004

(87) PCT Pub. No.: WO03/104454

PCT Pub. Date: Dec. 18, 2003

(65) Prior Publication Data

US 2005/0124056 A1  Jun. 9, 2005

(30) Foreign Application Priority Data

Jun. 6, 2002 (JP) ............................. 2002-165612
Mar. 7, 2003 (JP) ............................. 2003-060749

(51) Int. Cl.
*C12Q 1/68* (2006.01)
*C12N 9/02* (2006.01)
*C12N 15/70* (2006.01)
*C12P 21/06* (2006.01)
*C07H 21/04* (2006.01)

(52) U.S. Cl. .................. 435/6; 435/189; 435/69.1; 435/320.1; 536/23.2

(58) Field of Classification Search ................ 435/189, 435/23.2
See application file for complete search history.

(56) References Cited

FOREIGN PATENT DOCUMENTS

| WO | WO 00/28031 A2 | 5/2000 |
|----|----------------|--------|
| WO | WO 01/96390 A2 | 12/2001 |
| WO | WO 02/06515 A2 | 1/2002 |
| WO | WO 02/081703 A2 | 10/2002 |
| WO | WO 02/103028 A2 | 12/2002 |

OTHER PUBLICATIONS

Banfi et al., "Two novel proteins activate superoxide generation by the NADPH oxidase NOX1", J. Biol. Chem., 278(6): 3510-3513, Feb. 7, 2003.*
Botond Banfi et al., "A Mammalian H+ Channel Generated Through Alternative Splicing of the NADPH Oxidase Homolog NOH-1", SCIENCE (2000), vol. 287, pp. 138-142.
Young-Ah Suh et al., "Cell transporation by the superoxide-generating oxidase MX1", NATURE (1999), vol. 401, pp. 79-82.
Elena A. Ostrakhovitch et al., "Oxidative stress in rheumatoid arthritis leukocytes: suppression by rutin and other antioxidants and chelators", Biochemical Pharmacology (2001), vol. 62, No. 6, pp. 743-746.
Dan Sorescu et al., "Superoxide Production and Expression of Nox Family Proteins in Human Atherosclerosis", (2002) Circulation, vol. 105, No. 12, pp. 1429-1435.
Supplementary Partial European Search Report dated Aug. 9, 2005.

* cited by examiner

*Primary Examiner*—Rebecca E. Prouty
*Assistant Examiner*—Iqbal Chowdhury
(74) *Attorney, Agent, or Firm*—Sughrue Mion, PLLC

(57) ABSTRACT

There is disclosed an oxidase gene useful for the diagnosis of RA and the screening of a substance for the treatment of RA and/or a substance for the treatment of osteoarthritis. Also, an inspection method useful as a diagnosis method for RA is disclosed. Additionally, there is disclosed a method for screening a substance for the treatment of RA and/or a substance for the treatment of osteoarthritis, using the aforementioned novel oxidase gene. Also disclosed is a method for producing a pharmaceutical composition for the treatment of RA and/or the treatment of osteoarthritis which comprises an inhibitor of the aforementioned oxidase, which is obtainable by the aforementioned screening method, as an active ingredient.

2 Claims, 3 Drawing Sheets

SEQUENCE LISTING

<160> NUMBER OF SEQ ID NOS: 13

<210> SEQ ID NO 1
<211> LENGTH: 1548
<212> TYPE: DNA
<213> ORGANISM: Homo sapiens
<220> FEATURE:
<221> NAME/KEY: CDS
<222> LOCATION: (1)..(1548)

<400> SEQUENCE: 1

```
atg gga aac tgg gtg gtt aac cac tgg ttt tca gtt ttg ttt ctg gtt        48
Met Gly Asn Trp Val Val Asn His Trp Phe Ser Val Leu Phe Leu Val
1               5                  10                  15 gtt tgg tta ggg ctg aat gtt ttc ctg ttt gtg gat gcc ttc ctg aaa        96
Val Trp Leu Gly Leu Asn Val Phe Leu Phe Val Asp Ala Phe Leu Lys
            20                  25                  30 tat gag aag gcc gac aaa tac tac tac aca aga aaa atc ctt ggg tca       144
Tyr Glu Lys Ala Asp Lys Tyr Tyr Tyr Thr Arg Lys Ile Leu Gly Ser
        35                  40                  45 aca ttg gcc tgt gcc cga gcg tct gct ctc tgc ttg aat ttt aac agc       192
Thr Leu Ala Cys Ala Arg Ala Ser Ala Leu Cys Leu Asn Phe Asn Ser
    50                  55                  60 acg ctg atc ctg ctt cct gtg tgt cgc aat ctg ctg tcc ttc ctg agg       240
Thr Leu Ile Leu Leu Pro Val Cys Arg Asn Leu Leu Ser Phe Leu Arg
65                  70                  75                  80 ggc acc tgc tca ttt tgc agc cgc aca ctg aga aag caa ttg gat cac       288
Gly Thr Cys Ser Phe Cys Ser Arg Thr Leu Arg Lys Gln Leu Asp His
                85                  90                  95 aac ctc acc ttc cac aag ctg gtg gcc tat atg atc tgc cta cat aca       336
Asn Leu Thr Phe His Lys Leu Val Ala Tyr Met Ile Cys Leu His Thr
            100                 105                 110 gct att cac atc att gca cac ctg ttt aac ttt gac tgc tat agc aga       384
Ala Ile His Ile Ile Ala His Leu Phe Asn Phe Asp Cys Tyr Ser Arg
        115                 120                 125 agc cga cag gcc aca gat ggc tcc ctt gcc tcc att ctc tcc agc cta       432
Ser Arg Gln Ala Thr Asp Gly Ser Leu Ala Ser Ile Leu Ser Ser Leu
```

```
                    130                 135                 140
tct cat gat gag aaa aag ggg ggt tct tgg cta aat ccc atc cag tcc      480
Ser His Asp Glu Lys Lys Gly Gly Ser Trp Leu Asn Pro Ile Gln Ser
145                 150                 155                 160 cga aac acg aca gtg gag tat gtg aca ttc acc agc gtt gct ggt ctc      528
Arg Asn Thr Thr Val Glu Tyr Val Thr Phe Thr Ser Val Ala Gly Leu
                165                 170                 175 act gga gtg atc atg aca ata gcc ttg att ctc atg gta act tca gct      576
Thr Gly Val Ile Met Thr Ile Ala Leu Ile Leu Met Val Thr Ser Ala
            180                 185                 190 act gag ttc atc cgg agg agt tat ttt gaa gtc ttc tgg tat act cac      624
Thr Glu Phe Ile Arg Arg Ser Tyr Phe Glu Val Phe Trp Tyr Thr His
        195                 200                 205 cac ctt ttt atc ttc tat atc ctt ggc tta ggg att cac ggc att ggt      672
His Leu Phe Ile Phe Tyr Ile Leu Gly Leu Gly Ile His Gly Ile Gly
    210                 215                 220 gga att gtc cgg ggt caa aca gag gag agc atg aat gag agt cat cct      720
Gly Ile Val Arg Gly Gln Thr Glu Glu Ser Met Asn Glu Ser His Pro
225                 230                 235                 240 cgc aag tgt gca gag tct ttt gag atg tgg gat gat cgt gac tcc cac      768
Arg Lys Cys Ala Glu Ser Phe Glu Met Trp Asp Asp Arg Asp Ser His
                245                 250                 255 tgt agg cgc cct aag ttt gaa ggg cat ccc cct gag tct tgg aag tgg      816
Cys Arg Arg Pro Lys Phe Glu Gly His Pro Pro Glu Ser Trp Lys Trp
            260                 265                 270 atc ctt gca ccg gtc att ctt tat atc tgt gaa agg atc ctc cgg ttt      864
Ile Leu Ala Pro Val Ile Leu Tyr Ile Cys Glu Arg Ile Leu Arg Phe
        275                 280                 285 tac cgc tcc cag cag aag gtt gtg att acc aag gtt gtt atg cac cca      912
Tyr Arg Ser Gln Gln Lys Val Val Ile Thr Lys Val Val Met His Pro
    290                 295                 300 tcc aaa gtt ttg gaa ttg cag atg aac aag cgt ggc ttc agc atg gaa      960
Ser Lys Val Leu Glu Leu Gln Met Asn Lys Arg Gly Phe Ser Met Glu
305                 310                 315                 320 gtg ggg cag tat atc ttt gtt aat tgc ccc tca atc tct ctc ctg gaa     1008
Val Gly Gln Tyr Ile Phe Val Asn Cys Pro Ser Ile Ser Leu Leu Glu
                325                 330                 335 tgg cat cct ttt act ttg acc tct gct cca gag gaa gat ttc ttc tcc     1056
Trp His Pro Phe Thr Leu Thr Ser Ala Pro Glu Glu Asp Phe Phe Ser
            340                 345                 350 att cat atc cga gca gca ggg gac tgg aca gaa aat ctc ata agg gct     1104
Ile His Ile Arg Ala Ala Gly Asp Trp Thr Glu Asn Leu Ile Arg Ala
        355                 360                 365 ttc gaa caa caa tat tca cca att ccc agg att gaa gtg gat ggt ccc     1152
Phe Glu Gln Gln Tyr Ser Pro Ile Pro Arg Ile Glu Val Asp Gly Pro
    370                 375                 380 ttt ggc aca gcc agt gag gat gtt ttc cag tat gaa gtg gct gtg ctg     1200
Phe Gly Thr Ala Ser Glu Asp Val Phe Gln Tyr Glu Val Ala Val Leu
385                 390                 395                 400 gtt gga gca gga att ggg gtc acc ccc ttt gct tct atc ttg aaa tcc     1248
Val Gly Ala Gly Ile Gly Val Thr Pro Phe Ala Ser Ile Leu Lys Ser
                405                 410                 415 atc tgg tac aaa ttc cag tgt gca gac cac aac ctc aaa aca aaa aag     1296
Ile Trp Tyr Lys Phe Gln Cys Ala Asp His Asn Leu Lys Thr Lys Lys
            420                 425                 430 gtt ggt cat gca gca tta aac ttt gac aag gcc act gac atc gtg aca     1344
Val Gly His Ala Ala Leu Asn Phe Asp Lys Ala Thr Asp Ile Val Thr
        435                 440                 445 ggt ctg aaa cag aaa acc tcc ttt ggg aga cca atg tgg gac aat gag     1392
```

```
Gly Leu Lys Gln Lys Thr Ser Phe Gly Arg Pro Met Trp Asp Asn Glu
    450                 455                 460 ttt tct aca ata gct acc tcc cac ccc aag tct gta gtg gga gtt ttc      1440
Phe Ser Thr Ile Ala Thr Ser His Pro Lys Ser Val Val Gly Val Phe
465                 470                 475                 480 tta tgt ggc cct cgg act ttg gca aag agc ctg cgc aaa tgc tgt cac      1488
Leu Cys Gly Pro Arg Thr Leu Ala Lys Ser Leu Arg Lys Cys Cys His
                485                 490                 495 cga tat tcc agt ctg gat cct aga aag gtt caa ttc tac ttc aac aaa      1536
Arg Tyr Ser Ser Leu Asp Pro Arg Lys Val Gln Phe Tyr Phe Asn Lys
            500                 505                 510 gaa aat ttt tga                                                      1548
Glu Asn Phe
        515

<210> SEQ ID NO 2
<211> LENGTH: 515
<212> TYPE: PRT
<213> ORGANISM: Homo sapiens

<400> SEQUENCE: 2

Met Gly Asn Trp Val Val Asn His Trp Phe Ser Val Leu Phe Leu Val
1               5                   10                  15

Val Trp Leu Gly Leu Asn Val Phe Leu Phe Val Asp Ala Phe Leu Lys
            20                  25                  30

Tyr Glu Lys Ala Asp Lys Tyr Tyr Thr Arg Lys Ile Leu Gly Ser
        35                  40                  45

Thr Leu Ala Cys Ala Arg Ala Ser Ala Leu Cys Leu Asn Phe Asn Ser
    50                  55                  60

Thr Leu Ile Leu Leu Pro Val Cys Arg Asn Leu Leu Ser Phe Leu Arg
65                  70                  75                  80

Gly Thr Cys Ser Phe Cys Ser Arg Thr Leu Arg Lys Gln Leu Asp His
                85                  90                  95

Asn Leu Thr Phe His Lys Leu Val Ala Tyr Met Ile Cys Leu His Thr
            100                 105                 110

Ala Ile His Ile Ile Ala His Leu Phe Asn Phe Asp Cys Tyr Ser Arg
        115                 120                 125

Ser Arg Gln Ala Thr Asp Gly Ser Leu Ala Ser Ile Leu Ser Ser Leu
    130                 135                 140

Ser His Asp Glu Lys Lys Gly Gly Ser Trp Leu Asn Pro Ile Gln Ser
145                 150                 155                 160

Arg Asn Thr Thr Val Glu Tyr Val Thr Phe Thr Ser Val Ala Gly Leu
                165                 170                 175

Thr Gly Val Ile Met Thr Ile Ala Leu Ile Leu Met Val Thr Ser Ala
            180                 185                 190

Thr Glu Phe Ile Arg Arg Ser Tyr Phe Glu Val Phe Trp Tyr Thr His
        195                 200                 205

His Leu Phe Ile Phe Tyr Ile Leu Gly Leu Gly Ile His Gly Ile Gly
    210                 215                 220

Gly Ile Val Arg Gly Gln Thr Glu Glu Ser Met Asn Glu Ser His Pro
225                 230                 235                 240

Arg Lys Cys Ala Glu Ser Phe Glu Met Trp Asp Asp Arg Asp Ser His
                245                 250                 255

Cys Arg Arg Pro Lys Phe Glu Gly His Pro Pro Glu Ser Trp Lys Trp
            260                 265                 270

Ile Leu Ala Pro Val Ile Leu Tyr Ile Cys Glu Arg Ile Leu Arg Phe
```

```
                    275                 280                 285
Tyr Arg Ser Gln Gln Lys Val Val Ile Thr Lys Val Val Met His Pro
    290                 295                 300

Ser Lys Val Leu Glu Leu Gln Met Asn Lys Arg Gly Phe Ser Met Glu
305                 310                 315                 320

Val Gly Gln Tyr Ile Phe Val Asn Cys Pro Ser Ile Ser Leu Leu Glu
                325                 330                 335

Trp His Pro Phe Thr Leu Thr Ser Ala Pro Glu Asp Phe Phe Ser
            340                 345                 350

Ile His Ile Arg Ala Ala Gly Asp Trp Thr Glu Asn Leu Ile Arg Ala
                355                 360                 365

Phe Glu Gln Gln Tyr Ser Pro Ile Pro Arg Ile Glu Val Asp Gly Pro
    370                 375                 380

Phe Gly Thr Ala Ser Glu Asp Val Phe Gln Tyr Glu Val Ala Val Leu
385                 390                 395                 400

Val Gly Ala Gly Ile Gly Val Thr Pro Phe Ala Ser Ile Leu Lys Ser
                405                 410                 415

Ile Trp Tyr Lys Phe Gln Cys Ala Asp His Asn Leu Lys Thr Lys Lys
    420                 425                 430

Val Gly His Ala Ala Leu Asn Phe Asp Lys Ala Thr Asp Ile Val Thr
            435                 440                 445

Gly Leu Lys Gln Lys Thr Ser Phe Gly Arg Pro Met Trp Asp Asn Glu
    450                 455                 460

Phe Ser Thr Ile Ala Thr Ser His Pro Lys Ser Val Val Gly Val Phe
465                 470                 475                 480

Leu Cys Gly Pro Arg Thr Leu Ala Lys Ser Leu Arg Lys Cys Cys His
            485                 490                 495

Arg Tyr Ser Ser Leu Asp Pro Arg Lys Val Gln Phe Tyr Phe Asn Lys
                500                 505                 510

Glu Asn Phe
    515

<210> SEQ ID NO 3
<211> LENGTH: 28
<212> TYPE: DNA
<213> ORGANISM: Homo sapiens

<400> SEQUENCE: 3
gaagggctcc aaaccacctc ttgacaat                                    28

<210> SEQ ID NO 4
<211> LENGTH: 30
<212> TYPE: DNA
<213> ORGANISM: Homo sapiens

<400> SEQUENCE: 4
aaaatgcaga ttaccgtcct tattccttaa                                  30

<210> SEQ ID NO 5
<211> LENGTH: 27
<212> TYPE: DNA
<213> ORGANISM: Homo sapiens

<400> SEQUENCE: 5
aaaacaaaaa aggttggtca tgcagca                                     27

<210> SEQ ID NO 6
```

-continued

```
<211> LENGTH: 21
<212> TYPE: DNA
<213> ORGANISM: Homo sapiens

<400> SEQUENCE: 6
tcaaaaattt tctttgttga a                                              21

<210> SEQ ID NO 7
<211> LENGTH: 20
<212> TYPE: DNA
<213> ORGANISM: Homo sapiens

<400> SEQUENCE: 7
accacagtcc atgccatcac                                                20

<210> SEQ ID NO 8
<211> LENGTH: 20
<212> TYPE: DNA
<213> ORGANISM: Homo sapiens

<400> SEQUENCE: 8
tccaccaccc tgttgctgta                                                20

<210> SEQ ID NO 9
<211> LENGTH: 19
<212> TYPE: DNA
<213> ORGANISM: Homo sapiens

<400> SEQUENCE: 9
attgcctctg aattcaaca                                                 19

<210> SEQ ID NO 10
<211> LENGTH: 18
<212> TYPE: DNA
<213> ORGANISM: Homo sapiens

<400> SEQUENCE: 10
agtattgatg atcttaaa                                                  18

<210> SEQ ID NO 11
<211> LENGTH: 20
<212> TYPE: DNA
<213> ORGANISM: Mus musculus

<400> SEQUENCE: 11
ttgtaccttg tctactccca                                                20

<210> SEQ ID NO 12
<211> LENGTH: 19
<212> TYPE: DNA
<213> ORGANISM: Mus musculus

<400> SEQUENCE: 12
acagagcaat gactccaaa                                                 19

<210> SEQ ID NO 13
<211> LENGTH: 25
<212> TYPE: DNA
<213> ORGANISM: Homo sapiens

<400> SEQUENCE: 13
aaaacaaaaa agatctattt ctact                                          25
```

OXIDASE

TECHNICAL FIELD

This invention relates to a polypeptide as a novel oxidase, a polynucleotide coding for the polypeptide, a vector comprising the polynucleotide, a transformed cell comprising the vector, an inspection method useful for diagnosing rheumatoid arthritis (to be referred to as RA) and a method for screening a substance for the treatment of RA and/or a substance for the treatment of osteoarthritis.

BACKGROUND OF THE INVENTION

Nicotinamide adenine dinucleotide phosphate (NADPH) oxidase is an enzyme which forms an reactive oxygen species (to be referred to as ROS) by receiving an electron from NADPH and finally delivering it to an oxygen molecule. Physiologically, the aforementioned enzyme mainly existing in phagocytes is taking an important role in a defense system in a living body against invasion of foreign bodies such as microorganisms, which is sterilization of them by forming ROS and the like. However, it is known that excess formation of ROS by the enzyme causes digestion of protein and DNA and the damage to membranes by lipid peroxide and thereby becomes the cause of disorders of cells and tissues and furthermore of various diseases including inflammatory diseases, vascular diseases, neurodegenerative diseases, cancers, heart diseases and the like (cf. non-patent reference 1 and non-patent reference 2). However, since expression of the NADPH oxidase which forms ROS is systemically distributed, there is a possibility of causing side effects when this is considered as a target of drug discovery.

On the other hand, an NADPH oxidase family, NOX1, distributing in non-phagocytic cells has been identified by the recent studies, and it has been reported that ROS is tissue-specifically formed in cells other than phagocyte (cf. non-patent reference 3). It has been reported that NOX1 is present in the large intestine in a large amount and causes cell proliferation and upregulation of various genes, suggesting that it is concerned in various diseases in the large intestine.

There are various reports on the amino acid sequences having high homology with NOX1 and nucleotide sequences coding for the sequences. These are registered at data bases as accession numbers AF166328 (GENPEPT), AJ438989 (GENPEPT), HSA438989 (GENBANK), AF127763 (GENPEPT), AF166327 (GENPEPT), Q9YSS8 (SWISSPROT) and Q9WV87 (SWISSPROT), and reported in the non-patent reference 4, patent reference 1 and patent reference 2. The molecules are described in these references as factors which exist and function in the large intestine and are useful for the diagnosis of large bowel cancer, development of a therapeutic agent for large bowel cancer and the like. A sequence having high homology with NOX1 is described in the patent reference 3 which describes that the sequence is concerned in the production of active oxygen and useful for the treatment of diseases related to abnormal cell growth such as cancers and prostatic hypertrophy.

RA is a chronic inflammatory disease of unknown origin, which has the mainlocus of lesion in the synovial tissue and causes flare, swelling, heat sensation, pain, movement restriction and destruction of joints. Overproduction of inflammatory cytokines such as interleukin-1 (IL-1), interleukin-6 (IL-6), interleukin-8 (IL-8), interleukin-12 (IL-12), interleukin-15 (IL-15), interleukin-18 (IL-18), tumor necrosis factor-α (TNF-α) and the like, nitric oxide (NO), prostaglandins (PGs) and the like is known in the synovial tissue of RA (cf. non-patent reference 5). In recent years, a therapeutic method aimed at IL-1, IL-6 or TNF-α has been developed using a monoclonal antibody and a soluble receptor, and its efficacy is drawing attention (cf. non-patent reference 6). However, there is a group of patients in which complete remission cannot be introduced by the conventional therapeutic method which uses a therapeutic target molecule as the mechanism (cf. non-patent reference 7). Accordingly, identification of a new therapeutic target molecule different from the already known reports is expected.

It is known that ROS activates NFκB which is a transcription factor that expresses and induces various molecules, via oxidation-reduction control (cf. non-patent reference 8). Among the molecules of which expression is induced by NFκB, TNFα known as an inflammatory cytokine is also broadly acknowledged in the clinical field as the target of anti-RA agents (cf. non-patent reference 9), and COX-2 known as a prostaglandin synthesizing enzyme is also broadly acknowledged in the clinical field as the target of agents for treating RA and osteoarthritis (cf. non-patent reference 10).

On the other hand, standards on the classification of RA have been defined from an American university (cf. non-patent reference 11). However, since these standards are merely landmarks and disease condition patterns thereof are various, it has been considered that diagnosis of RA, particularly quantitative and convenient diagnosis thereof, is difficult to carry out. A quantitative and convenient diagnosis method for RA has been expected.

(Patent reference 1) International publication WO 02/06515 pamphlet (Patent reference 2) International publication WO 01/96390 pamphlet (Patent reference 3) International publication WO 00/28031 pamphlet (Non-patent reference 1) *Trends in Pharmacological Science*, (USA), 2000, vol. 21, pp. 119–120

(Non-patent reference 2) *Federation of European Biochemical Society*, (Germany), 1991, vol. 281, pp. 9–19

(Non-patent reference 3) *Nature*, (England), 1999, vol. 401, pp. 79–82

(Non-patent reference 4) *Science*, (USA), 2000, vol. 287, p. 138

(Non-patent reference 5) *The Journal of Experimental Medicine*, (USA), 1991, vol. 173, pp. 569–574

(Non-patent reference 6) *Current Pharmaceutical Biotechnology*, (USA), 2000, vol. 1, pp. 217–233

(Non-patent reference 7) *Nature Reviews Immunology*, (England), 2002, vol. 2, pp. 364–371

(Non-patent reference 8) *The Journal of Biological Chemistry*, (USA), 1993, vol. 268, pp. 11380–11388

(Non-patent reference 9) *Arthritis & Rheumatism*, (USA), 1999, vol. 36, pp. 1681–1690

(Non-patent reference 10) *Arthritis & Rheumatism*, (USA), 1998, vol. 41, pp. 1591–1602

(Non-patent reference 11) "*Medicine*", edited by J. Axford, (USA), Blackwell Science, 1996, pp. 3.18–3.22

DISCLOSURE OF THE INVENTION

The inventor of the present invention have conducted intensive studies and as a result succeeded in obtaining complete length sequence of a gene of a novel oxidase (to be referred to as NOX1-b) from synovial cells derived from a human RA patient. Also, it was found that the NOX1-b gene is not expressed in synovial cells derived from healthy persons but expressed specifically in synovial cells derived from RA patients to make an inspection method useful as a diagnosis method for RA possible by the use of NOX1-b-specific polymerase chain reaction (PCR) primers. Additionally, a method for screening a substance for the treatment of RA and/or a substance for the treatment of osteoarthritis was constructed by using the NOX1-b gene. It was revealed that expression of COX-2 known as a target of the treating agents for RA and osteoarthritis, and of TNFα known as a target of the treating agents for RA is significantly accelerated in cells expressing NOX1-b, in comparison with cells in which NOX1-b is not expressed, and that the expression acceleration of COX-2 and TNF-α is inhibited by an NOX1-b inhibitor. As a result of these findings, the present invention has been accomplished by providing a novel oxidase NOX1-b, an inspection method useful for the diagnosis of RA and a method for screening a substance for the treatment of RA and/or a substance for the treatment of osteoarthritis.

That is, the present invention relates to (1) (i) A polypeptide which comprises the amino acid sequence represented by SEQ ID NO:2, and which is expressed specifically in rheumatoid arthritis patients, or (ii) a polypeptide which comprises an amino acid sequence in which from 1 to several amino acids of the amino acid sequence represented by SEQ ID NO:2 are deleted and/or inserted, and which is expressed specifically in rheumatoid arthritis patients.

(2) A polypeptide consisting of the amino acid sequence represented by SEQ ID NO:2.

(3) A polynucleotide coding for the polypeptide according to (1) or (2).

(4) An expression vector comprising the polynucleotide according to (3).

(5) A cell transformed with the expression vector according to (4).

(6) A method for inspecting RA, comprising
  (i) a step of measuring an expression level in a subject of
    i) a gene comprising the nucleotide sequence according to (3), or
    ii) a gene comprising a nucleotide sequence of a polynucleotide coding for a polypeptide which comprises an amino acid sequence having 95% or more of homology with the amino acid sequence represented by SEQ ID NO:2 and which is expressed specifically in RA patients, and
  (ii) a step of comparing it with an expression level of the gene in a healthy person.

(7) A rheumatoid arthritis inspection kit which comprises forward and reverse primers designed to specifically amplify
  (i) a gene comprising the nucleotide sequence according to (3), or
  (ii) a gene comprising a nucleotide sequence of a polynucleotide coding for a polypeptide which comprises an amino acid sequence having 95% or more of homology with the amino acid sequence represented by SEQ ID NO:2 and which is expressed specifically in RA patients.

(8) A method for screening a substance capable of inhibiting activity of a polypeptide, comprising (i) a step of allowing a substance to be tested to contact with a cell expressing the polypeptide according to (1) or (2) or a polypeptide which comprises an amino acid sequence having 95% or more of homology with the amino acid sequence represented by SEQ ID NO:2 and which is expressed specifically in RA patients, (ii) a step of analyzing whether or not activity of the polypeptide is inhibited, and (iii) a step of selecting a substance capable of inhibiting activity of the polypeptide.

(9) The screening method according to (8), wherein the substance which inhibits the activity of the polypeptide according to (1) or (2), or of a polypeptide which comprises an amino acid sequence having 95% or more of homology with the amino acid sequence represented by SEQ ID NO:2 and which is expressed specifically in RA patients is a substance for the treatment of rheumatoid arthritis and/or a substance for the treatment of osteoarthritis.

(10) A method for producing a pharmaceutical composition for the treatment of RA and/or the treatment of osteoarthritis, comprising
  a step of carrying out screening with the use of the screening method according to (8) or (9), and
  a step of formation using a substance obtained by the screening.

Although there are no reports on sequences identical to the NOX1-b complete length amino acid sequence comprising SEQ ID NO:2 and a nucleotide sequence coding for the sequence, there are various reports on amino acid sequences having high homology therewith and nucleotide sequences coding for the sequences. A sequence in which 1 amino acid or 1 base is different from the NOX1-b sequence of the present invention is registered at the databases GENPEPT and GENBANK as a accession number AF166328. Also, sequences in which 2 amino acids or 4 bases are different from the NOX1-b sequence of the present invention are registered at the databases of GENPEPT and GENBANK as accession numbers AJ438989 and HSA438989, respectively. However, there is no description in any one of them suggesting that proteins comprising these sequences are expressed in the synovial cells of RA patients and become the target of the treatment of RA. Proteins having high homology with the polypeptide of the present invention (49 amino acids are inserted between the 432nd and 433rd positions of SEQ ID NO:2) have been registered at the data base of GENPEPT as accession numbers AF127763 and AF166327, and at the data base of SWISSPROT as accession numbers Q9Y5S8 and Q9WV87, respectively, and reported in "Science, 287, 138 (2000)", "Nature, 401, 79 (1999)" and WO 02/06515. In addition, a protein having high homology with the polypeptide of the present invention (16 amino acids are inserted between the 80th and 81st positions of SEQ ID NO:2, and 49 amino acids are inserted between the 432nd and 433rd positions) has been reported in WO 01/96390. However, the molecule is described in these references as a factor which exists and functions in the large intestine and is useful for the diagnosis of large bowel cancer, development of a therapeutic agent for large bowel cancer and the like, while its relation to RA is not described therein. A protein having high homology with the polypeptide of the present invention (49 amino acids are inserted between the 432nd and 433rd positions of SEQ ID NO:2) has been reported in WO 00/28031, and it is described that the sequence is concerned with the formation of reactive oxygen. It is described that the aforementioned protein is specifically and frequently expressed in the large intestine and useful for the treatment of diseases in which abnormal cell growth is concerned, such as cancers and prostatic hypertrophy. Although it is necessary to diagnose RA by synovial membrane, expression of the aforementioned protein in synovial tissue was not confirmed in the international publication pamphlet, and whether or not it is specifically expressed in RA patients is not verified, too. Additionally, whether or not the aforementioned protein accelerates expression of TNF-α and COX-2 as the cause of RA is not verified too, and there is no information that the protein is useful for the inspection of RA and as a target of the treatment of RA.

Thus, the fact that the polypeptide of the present invention is not present in the healthy person-derived synovial cells but specifically present in the RA patient-derived synovial cells and the polypeptide of the present invention becomes a target of the treatment of RA is a knowledge found for the first time by the inventor of the present invention, and the method for inspecting RA using the same and the method for screening a substance for the treatment of RA are inventions carried out for the first time by the inventor of the present invention.

BEST MODE FOR CARRYING OUT THE INVENTION

Figure 1:
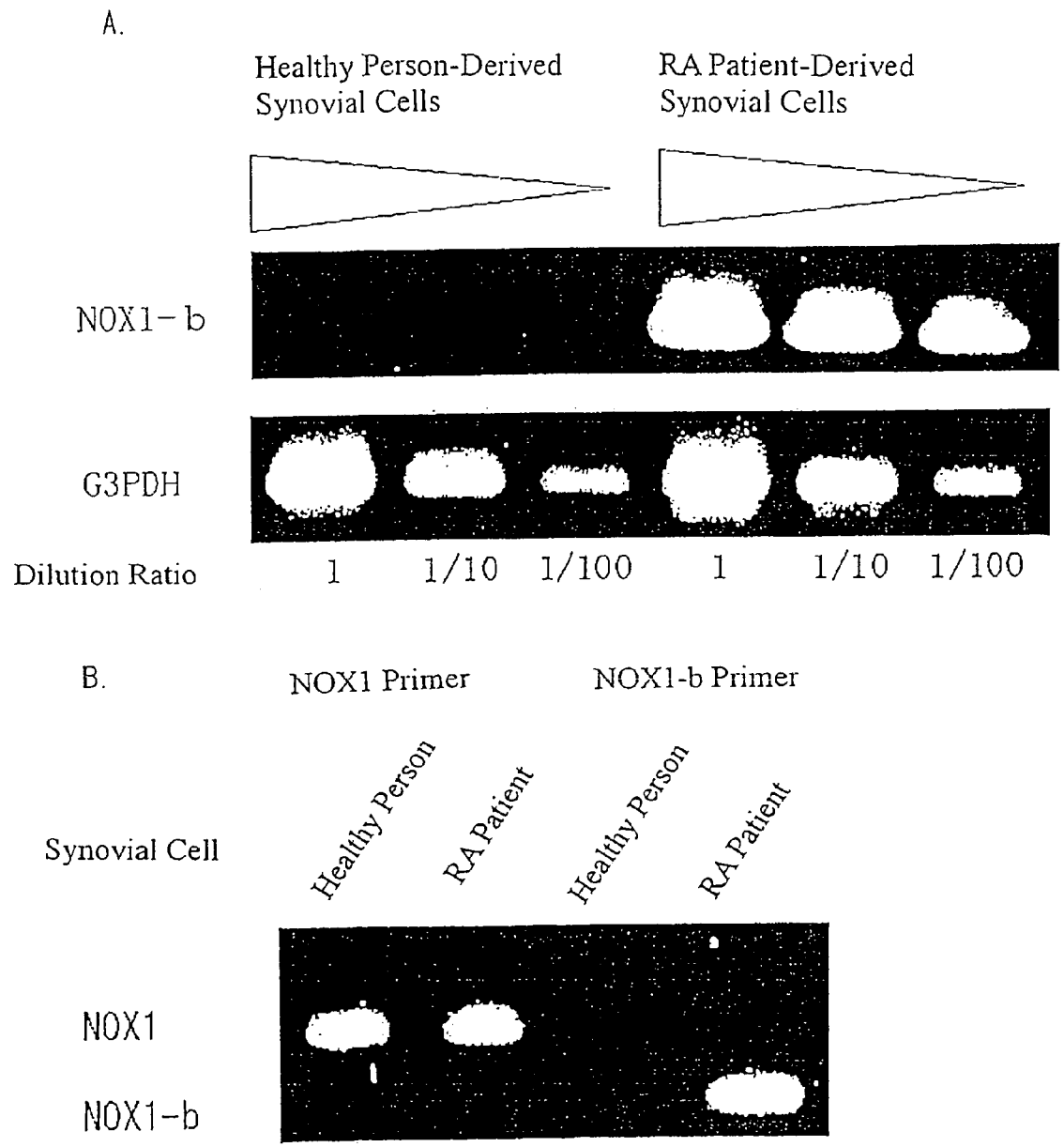
FIG. 1 shows increase in the expression of NOX1-b mRNA in RA patient-derived synovial cells.

According to the present invention, "RA" is used as the abbreviation of "rheumatoid arthritis". Conventionally, Japanese translation of RA was "Mansei kansetsu riumachi (chronic rheumatoid arthritis)", but it was announced by The Japan Rheumatism Association in 2002 that the Japanese version of RA is changed from "Mansei kansetsu riumachi (chronic rheumatoid arthritis)" to "Kansetsu riumachi(rheumatoid arthritis)", so that the terminology was changed accordingly in this specification.

<Polypeptide and Polynucleotide of the Invention>

In the polypeptide of the present invention, (1) a polypeptide consisting of the amino acid sequence represented by SEQ ID NO:2; and (2) a polypeptide which comprises the amino acid sequence represented by SEQ ID NO:2, and which is expressed specifically in RA patients, or a polypeptide which comprises an amino acid sequence in which from 1 to several amino acids of the amino acid sequence represented by SEQ ID NO:2 are deleted and/or inserted, and which is expressed specifically in RA patients; (to be called functionally equivalent variant hereinafter)

are included.

As the "functionally equivalent variant of the present invention", "a polypeptide which comprises the amino acid sequence represented by SEQ ID NO:2, and which is expressed specifically in RA patients", or "a polypeptide which comprises an amino acid sequence in which from 1 to 10, preferably from 1 to 7 and more preferably from 1 to 5, amino acids of the amino acid sequence represented by SEQ ID NO:2 are deleted and/or inserted, and which is expressed specifically in RA patients" is desirable.

The polypeptides of the present invention have been described in the foregoing, the polypeptide consisting of the amino acid sequence represented by SEQ ID NO:2 and the functionally equivalent variant of the present invention are generally referred to as "the polypeptide of the present invention" hereinafter. Among the "polypeptides of the present invention", a protein which is a polypeptide comprising the amino acid sequence represented by SEQ ID NO:2 is called "NOX1-b protein".

As the polypeptide of the present invention, "a polypeptide consisting of the amino acid sequence represented by SEQ ID NO:2" and "a polypeptide which comprises the amino acid sequence represented by SEQ ID NO:2, and which is expressed specifically in RA patients, or a polypeptide which comprises an amino acid sequence in which from 1 to 10, preferably from 1 to 7 and more preferably from 1 to 5, amino acids of the amino acid sequence represented by SEQ ID NO:2 are deleted and/or inserted, and which is specifically expressed in RA patients" are desirable, and "a polypeptide comprising the amino acid sequence represented by SEQ ID NO:2" is more desirable.

Additionally, the polynucleotide of the present invention may be any nucleotide sequence coding for the NOX1-b protein represented by the amino acid sequence described in SEQ ID NO:2 or a functionally equivalent variant thereof. Preferred is a polynucleotide having a nucleotide sequence coding for the amino acid sequence described in SEQ ID NO:2, and more preferred is the nucleotide sequence described in SEQ ID NO:1.

The production method of the polynucleotide of the present invention is not particularly limited, but for example includes (1) a method using PCR, (2) a method using an usual genetic engineering technique (namely a method for selecting a transformant containing an amino acid sequence of interest from transformants which is transformed with a cDNA library) or (3) a chemical synthesis method and the like. Each of the production methods can be carried out in the same manner as described in WO 01/34785 in which invention of a novel enzyme is disclosed. However, the "novel protein of the invention" according to the aforementioned patent application specification is interpreted as a polypeptide of the present invention (e.g., NOX1-b protein), and the "gene of the invention" as a polynucleotide of the present invention (e.g., NOX1-b).

Illustratively, according to the method which using PCR, the polynucleotide of the present invention can be produced, for example, by the procedure described in the a) First production method in 1) Production method of protein gene in "Mode for Carrying Out the Invention" of the aforementioned patent reference. Firstly, mRNA is extracted from a cell or tissue having the ability to produce the protein of the present invention, such as a human RA patient-derived synovial membrane. Next, a first strand cDNA can be synthesized by a reverse transcriptase reaction using the mRNA in the presence of a random primer or an oligo(dT) primer. The polynucleotide of the present invention or a part thereof is obtainable by subjecting the thus obtained first strand cDNA to a polymerase chain reaction (PCR) using two primers interposing a partial region of the objective gene. More illustratively, the objective gene is amplified, for example, by the method described in Example 1 using the sequences represented by SEQ ID NO:5 and SEQ ID NO:6 as the primers. Subsequently, by confirming whether or not the thus amplified gene is expressed specifically in RA patients for example by the method described in Example 4, the gene which is RA patient-specifically expressed in comparison with a healthy parson can be selected as the polynucleotide of the present invention.

According to the method using a usual genetic engineering technique, the polynucleotide of the present invention can be produced, for example, by the procedure described in the b) Second production method in 1) Production method of protein gene in "Mode for Carrying Out the Invention" of the aforementioned patent reference.

According to the method using a chemical synthesis method, the polynucleotide of the present invention can be produced, for example, by the methods described in the c) Third production method and d) Fourth production method in 1) Production method of protein gene in "Mode for Carrying Out the Invention" of the aforementioned patent reference.

The methods for producing the expression vector, host cell and protein of the present invention can be carried out, for example, by the methods described in 2) Production methods of the vector of the present invention, the host cell of the present invention and the recombinant protein of the present invention in "Mode for Carrying Out the Invention" of the aforementioned patent reference. More illustratively, the expression vector of the present invention can be produced by the method described in Example 2 using a mammalian cell expression vector pcDNA3.1/HisB, and the host cell and protein of the present invention by the method described in Example 3 in which an NIH3T3 cell is transfected using a transfection reagent.

Since the polynucleotide of the present invention can be used by itself as a hybridization probe in the following RA inspection method, it is useful for the inspection of RA. Additionally, the polynucleotide of the present invention can be used in preparing an antibody capable of specifically recognizing the polynucleotide of the present invention and as a control in detecting and/or determining its expression level.

Inspection Method of RA/Kit for RA Inspection

As is described in the following, since it was found that NOX1-b was not expressed in samples derived from healthy persons, but NOX1-b was specifically expressed in samples derived from RA patients, the RA disease can be detected by using the expression. Illustratively, an embodiment containing the following steps can be exemplified. Namely,

[1] a step in which measuring the expression level in a subject of (1) a gene comprising the nucleotide sequence of the polynucleotide of the present invention (namely, a gene comprising a nucleotide sequence of a polynucleotide coding for i) a polypeptide which comprises the amino acid sequence represented by SEQ ID NO:2 and which is expressed specifically in RA patients, ii) a polypeptide which comprises an amino acid sequence in which from 1 to several amino acids of the amino acid sequence represented by SEQ ID NO:2 are deleted and/or inserted and which is expressed specifically in RA patients, or iii) a polypeptide comprising the amino acid sequence represented by SEQ ID NO:2), or (2) a gene comprising a nucleotide sequence of a polynucleotide coding for a polypeptide which comprises an amino acid sequence having 95% or more of homology with the amino acid sequence represented by SEQ ID NO:2 and which is expressed specifically in RA patients and

[2] a step in which the result is compared with the expression level of the aforementioned gene in a healthy person.

The "polypeptide which comprises an amino acid sequence having 90% or more of homology with the amino acid sequence represented by SEQ ID NO:2 and which is specifically expressed in RA patients" according to the aforementioned (2) is called as "homologous polypeptide according to the present invention". Although the homologous polypeptide according to the present invention is not particularly limited, so far as it is "a polypeptide which comprises an amino acid sequence having 95% or more of homology with the amino acid sequence represented by SEQ ID NO:2 and which is expressed specifically in RA patients", a polypeptide which comprises an amino acid sequence preferably having 97% or more, more preferably 99% or more, of the homology is desirable.

In this connection, the aforementioned "homology" according to this specification means the Identities value obtained by the BLAST (Basic local alignment search tool; Altschul, S. F. et al., *J. Mol. Biol.*, 215, 403–410, 1990) retrieval. With regard to the parameters in this case, "blastp" is used as the "program name", the "Gap insertion Cost value" by "0", the "Gap elongation Cost value" by "0", and "BLOSUM62" as the "Matrix", respectively as the pair-wise alignment parameters.

The homologous polypeptide according to the present invention can be produced by the same method for the production of the polypeptide of the present invention. The polypeptide of the present invention and the homologous polypeptide according to the present invention are generally referred to as the polypeptide for screening of the present invention. As the polypeptide for screening of the present invention, a polypeptide comprising the amino acid sequence represented by SEQ ID NO:2 is particularly desirable.

The gene expression level according to the RA inspection method of the present invention include transcription of the gene into mRNA and its translation into protein. Accordingly, the RA inspection method by the present invention is carried out based on the comparison of the expression level of mRNA which corresponds to a polynucleotide coding for the polypeptide for screening of the present invention (e.g., NOX1-b gene), or the expression level of a protein encoded by the gene.

The method for measuring expression level of a gene (e.g., NOX1-B gene) in the step [1] can be carried out in accordance with a conventionally known gene analyzing method. For example, a hybridization technique in which a nucleic acid capable of hybridizing with the NOX1-b gene is used as the probe, a gene amplification technique in which DNA fragments capable of hybridizing with the NOX1-b gene are used as the primers, and the like can be used. Illustratively, it can be measured using a synovial cell-derived nucleic acid, such as mRNA or the like, obtained from a subject. With regard to the measurement of mRNA, it can be measured by a gene amplification reaction method using primers designed in such a manner that they can specifically amplify a polynucleotide coding for the polypeptide for screening of the present invention (e.g., NOX1-b sequence). Although the gene amplification reaction method is not particularly limited, a PCR method, an nucleic acid amplification method using a RNA polymerase and the like can be employed. More illustratively, it can be carried out by the method described in Example 4. The primers to be used in the RA inspection method, or the primers to be contained in the kit for RA inspection of the present invention, are not particularly limited as far as they can specifically amplify a polynucleotide coding for the polypeptide for screening of the present invention (e.g., NOX1-b sequence), and they can be designed based on a polynucleotide coding for the polypeptide for screening of the present invention (e.g., NOX1-b nucleotide sequence). Preferred are the oligonucleotides described in SEQ ID NO:5 and SEQ ID NO:6.

The RA inspection which uses a hybridization technique can be carried out, for example, by using a northern hybridization, a dot blotting, a DNA micro-array method and the like. It can also be carried out using gene amplification technique such as a RT-PCR. According to the RT-PCR method, it is possible to carry out more quantitative analysis of the expression of a gene comprising a polynucleotide coding for the polypeptide for screening of the present invention (e.g., NOX1-b gene), by using a PCR amplification monitoring (real time PCR) method in the gene amplification process. For example, ABI PRISM 7700 (Applied Biosystems) can be used as PCR amplification monitoring method.

Additionally, as the method in the step [1] for measuring the expression level of a gene containing the nucleotide sequence of a polynucleotide coding for the polypeptide for screening of the present invention, it is possible to employ a method in which the expression level is measured by detecting a protein comprising the polypeptide for screening of the present invention, preferably the NOX1-b protein. As such an inspection method, for example, it is able to use western blotting, immunoprecipitation, ELISA or the like, using a cell extract of synovial cells derived from a subject and using an antibody capable of binding to a protein comprising the polypeptide for screening of the present invention, preferably an NOX1-b protein and more preferably an antibody capable of specifically binding to NOX1-b.

The comparing method of the step [2] is not particularly limited, as far as the expression level obtained in the step [1] is compared with an expression level in a healthy person, and the comparison can be carried out, for example, by the method described in Example 4.

The RA inspection kit of the present invention contains at least forward and reverse primers designed in such a manner that it can specifically amplify a polynucleotide coding for the polypeptide for screening of the present invention. The forward and reverse primers include such as primers represented by the nucleotide sequences described in SEQ ID NO:5 and SEQ ID NO:6. Examples of other reagents which can be contained in the RA inspection kit of the present invention include those reagents such as those which are necessary for carrying out PCR (e.g., Taq polymerase, a nucleotide substrate, a buffer solution and the like).

Screening Method of the Invention

In the screening method of the present invention, a method for screening a substance capable of inhibiting activity of the polypeptide for screening of the present invention and a method for screening a substance for the treatment of RA and/or a substance for the treatment of osteoarthritis are included.

(1) A method for Screening a Substance Capable of Inhibiting Activity of the Polypeptide for Screening of the Present Invention The method for screening a substance capable of inhibiting activity of the polypeptide for screening of the present invention is not particularly limited so far as it contains the following steps (i) to (iii):

(i) a step of allowing a substance to be tested to contact with a cell expressing the polypeptide for screening of the present invention, (ii) a step of analyzing whether or not activity of the aforementioned polypeptide is inhibited, and (iii) a step of selecting a substance capable of inhibiting activity of the aforementioned polypeptide.

A substance capable of inhibiting activity of the polypeptide for screening of the present invention can be screened preferably by the method described in Example 5.

(2) A Method for Screening a Substance for the Treatment of RA and/or a Substance for the Treatment of Osteoarthritis As described in the column of Technical Field, TNF-α known as an inflammatory cytokine is also broadly acknowledged in the clinical field as the target of treating agents for RA, and COX-2 known as a prostaglandin synthesizing enzyme is also broadly acknowledged in the clinical field as the target of the agents for treating RA and osteoarthritis.

Accordingly, a substance for the treatment of RA and/or a substance for the treatment of osteoarthritis can be screened by selecting a substance which reduces expression of TNF-α or COX-2. As is shown in the following Examples, it was revealed that expression of COX-2 and expression of TNF-α are significantly accelerated in a cell which expresses NOX1-b which is one of the polypeptides of the present invention (Example 6 and Example 7). Additionally, since these COX-2 expression induction and TNF-α expression induction were inhibited by DPI which is an NOX1-b inhibitor, it was considered that expression of COX-2 and TNF-α was induced via a redox control by ROS derived from NOX1-b which is one of the polypeptides of the present invention. Based on a new knowledge found by the inventor of the present invention that the upregulation of COX-2 and/or TNF-α is inhibited through the inhibition of activity of the polypeptide of the present invention, it was considered that a substance capable of inhibiting activity of the polypeptide for screening of the present invention has the treating effect for RA. That is, a method for screening a substance capable of inhibiting activity of the polypeptide for screening of the present invention can be used as a method for screening a substance for the treatment of RA and/or a substance for the treatment of osteoarthritis.

The method for screening a substance for the treatment of RA and/or a substance for the treatment of osteoarthritis is not particularly limited so far as it contains the following steps (i) to (iii):

(i) a step of allowing a substance to be tested to contact with a cell expressing the polypeptide for screening of the present invention, (ii) a step of analyzing whether or not activity of the aforementioned polypeptide is inhibited, and (iii) a step of selecting which a substance capable of inhibiting activity of the aforementioned polypeptide.

Whether or not the substance obtained by the aforementioned screening method is a useful substance as the treating substance of RA can be judged by subjecting it to a conventionally known evaluation system of the treating agents of RA, or by subjecting to a modified evaluation system thereof. For example, confirming the RA-treating action can be carried out by a method which uses a collagen-induced arthritis model mouse (Fiona H. Duris et al., *Immunol. Immunopathol.*, 73, 11–18, 1994). Also, by subjecting the substance obtained by the aforementioned screening method to a conventionally known evaluation system of treating agents of osteoarthritis, whether or not it is an useful substance as a substance for the treatment of osteoarthritis can be judged.

Based on the difference in the method to be used for analyzing (measuring or detecting) activity of the polypeptide for screening of the present invention, the screening method of the present invention includes, for example, (a) a chemical-biochemical method, (b) a chemiluminescence method, (c) an electron spin resonance (ESR) method and the like. Each screening method is described in the following.

(a) Chemical-biochemical Method

A substance capable of inhibiting activity of the polypeptide for screening of the present invention and a substance for the treatment of RA and/or a substance for the treatment of osteoarthritis can be screened using a chemical-biochemical method. As the chemical-biochemical method includes, for example, (i) a screening method which uses a cytochrome C reduction method, (ii) a-screening method which uses reduction of nitroblue tetrazolium (NBT) and (iii) a screening method which uses reduction of a water-soluble tetrazolium salt. Detection by the cytochrome C reduction method uses an effect that oxidized cytochrome C changes to reduced counterpart having strong absorption at 550 nm when the former is reduced (J. M. MacCord and I. Fridovich, *J. Biol. Chem.*, 244, 6049 (1969)). The NBT reduction method uses an effect that NBT forms water-insoluble blue formazan (absorption maximum 560 nm) when it is reduced by $O_2^-$ (C. Beauchamp and I. Fridovich, *Anal. Biochem.*, 44, 276 (1971)).

Cells expressing the polypeptide for screening of the present invention are prepared. A substance to be tested is added thereto, an appropriate amount of a probe (e.g., cytochrome C) is further added thereto, and the mixture is incubated for a predetermined time. After the reaction, absorbance at 550 nm is measured. In case that conversion into the reduced form is inhibited when the substance to be tested is added, it can be judged that the aforementioned substance to be tested is a substance which inhibits activity of the polypeptide for screening of the present invention. It is desirable to carry out the screening method which uses a cytochrome C reduction method, as one of these methods, under the conditions described in Example 5. Regarding the substance which inhibits activity of the polypeptide for screening of the present invention, it is desirable to select a substance of 10 µM or less, preferably 1 µM or less, more preferably 0.1 µM or less.

(b) Chemiluminescence Method

Examples of the chemiluminescence method include (i) a screening method which uses a *Vargula hilgendorfii* luciferin derivative and (ii) a screening method which uses a luminol method. The *Vargula hilgendorfii* luciferin derivative forms an exited carbonyl compound by reacting with $O_2^-$ in an aqueous solution of about neutral range and generates strong luminescence at 380 nm when the latter is reaching a ground state, so that the phenomenon is used (Goto, T: *Pure Appl. Chem., Vol.* 17, 421–441, 1968). The detection by a luminol method uses a phenomenon that it forms an aminophthalic acid dianion (exited state) by undergoing oxidation by HOCl, $K_3Fe(CN)_6$, $K_2S_2O_8$, $Fe^{2+}$ salt, $Co^{3+}$ or the like in the presence of $O_2^-$ or $H_2O_2$ in an alkaline aqueous solution and generates luminescence when the latter is reaching a ground state (Roswell, D. F. et al., *Method in Enzymology, Vol.* 15, 409–423, 1972).

Cells expressing the polypeptide for screening of the present invention are prepared. A substance to be tested is added thereto and an appropriate amount of a probe (e.g., a *Vargula hilgendorfii* luciferin derivative) is further added thereto, and the mixture is allowed to undergo the reaction for a predetermined time. After the reaction, luminescence at 380 nm is measured. In case that the luminescence is inhibited when the substance to be tested is added, it can be judged that the aforementioned substance to be tested is a substance which inhibits activity of the polypeptide for screening of the present invention. With regard to the substance which inhibits activity of the polypeptide for screening of the present invention, it is desirable to select a substance of 10 µM or less, preferably 1 µM or less and more preferably 0.1 µM or less.

(c) Electron Spin Resonance (ESR) Method

The ESR signal of $O_2^-$ can be indirectly measured by the use of the spin-trap method. That is, the ESR method uses a process in which a radical species having a short life span is allowed to react with a trapping agent, and ESR spectrum of the thus formed stable radical is analyzed. The currently used spin-trapping agent having most high general purpose performance is 5,5-dimethyl-1-pyrroline-N-oxide (DMPO) (Y. Noda, K. Anzai, A. Mori, M. Kohno, M. Shinmei and L. Packer, *Biochem. Mol. Biol. Int.*, 42, 35 (1997)).

Cells expressing the polypeptide for screening of the present invention are prepared. A substance to be tested is added thereto, an appropriate amount of a spin-trapping agent (e.g., DMPO) is further added thereto, and the mixture is allowed to react for a predetermined time. After the reaction, spectral analysis of the radical-added product is carried out. In case that signal of the radical-added product is inhibited when the substance to be tested is added, it can be judged that the aforementioned substance to be tested is a substance which inhibits activity of the polypeptide for screening of the present invention. With regard to the substance which inhibits activity of the polypeptide for screening of the present invention, it is desirable to select a substance of 10 µM or less, preferably 1 µM or less and more preferably 0.1 µM or less.

Since the compound to be tested as the subject to be selected by the screening method of the present invention is not particularly limited, for example, various conventionally known compounds (including peptides) registered in chemical files, a group of compounds obtained by the combinatorial chemistry techniques (Terrett, N. K. et al., *Tetrahedron*, 51, 8135–8137, 1995) and a group of random peptides prepared by applying the phage display method (Felici, F. et al., *J. Mol. Biol.*, 222, 301–310, 1991) and the like can be used. Also, natural components derived from microorganisms, plants, marine organisms or animals (e.g., culture supernatants or tissue extracts) and the like can also be used as the subject of the screening. Additionally, compounds (including peptides) obtained by chemically or biologically modifying the compounds (including peptides) selected by the screening method of the present invention can also be used.

Method for Producing a Medicinal Composition for the Treatment of RA and/or the Treatment of Osteoarthritis In the present invention, a method for producing a medicinal composition for the treatment of RA and/or the treatment of osteoarthritis, comprising a step in which screening is carried out by using the screening method of the present invention and a step in which a substance obtained by the aforementioned screening is made into a pharmaceutical preparation.

The pharmaceutical preparation which comprises a substance obtained by the screening method of the present invention as the active ingredient can be prepared using generally used pharmaceutical carriers, fillers and/or other additives.

Examples of its administration include oral administration through such as tablets, pills, capsules, granules, fine subtilaes, powders and solutions for oral use, or parenteral administration through such as injections for intravenous injection, intramuscular injection and intraarticular injection, suppositories, percutaneous administration preparations, transmucosal administration preparations and the like. In the case of peptides which are digested in the stomach, parenteral administration such as intravenous injection is particularly desirable.

In the solid composition for oral administration, one or more active substances are mixed with at least one inert diluent such as lactose, mannitol, glucose, microcrystalline cellulose, hydroxypropylcellulose, starch, polyvinyl pyrrolidone, aluminum magnesium silicate or the like. In accordance with the usual method, the aforementioned composition may contain other additives than the inert diluent, such as a lubricant, a disintegrating agent, a stabilizing agent and a solubilizing or solubilization assisting agent. If necessary, tablets or pills may be subjected to sugar coating or coated with a film of a gastric or enteric substance.

The liquid composition for oral administration includes, for example, emulsions, solutions, suspensions, syrups, elixirs and the like and contains a generally used inert diluent such as purified water or ethanol. In addition to the inert diluent, the aforementioned composition may also includes other additives such as a moistening agent, a suspending agent, a sweetener, an aromatic and antiseptic.

The injections for parenteral administration includes aseptic aqueous or non-aqueous solutions, suspensions and emulsions. Examples of the diluent for use in the aqueous solutions and suspensions include distilled water for injection and physiological saline. Examples of the diluent for use in the non-aqueous solutions and suspensions include propylene glycol, polyethylene glycol, a plant oil (e.g., olive oil), an alcohol (e.g., ethanol), polysorbate 80 and the like. The aforementioned composition may further contains a moistening agent, an emulsifying agent, a dispersing agent, a stabilizing agent, a solubilizing or solubilization assisting agent, an antiseptic and the like. The aforementioned compositions can be sterilized by filtration through a bacteria retaining filter, blending of a germicide or irradiation. Alternatively, it can also be used by firstly making into a sterile solid composition and dissolving it in sterile water or a sterile medium for injection prior to its use.

The clinical dose can be optionally decided by taking into consideration strength of the activity of the active ingredient, namely the substance obtained by the screening method of the present invention, symptoms, age and sex of the subject to be administered and the like.

For example, in the case of oral administration, the dose is usually approximately from 0.1 to 100 mg, preferably from 0.1 to 50 mg, per day per adult (as 60 kg in body weight). In the case of parenteral administration, it is from 0.01 to 50 mg, preferably from 0.01 to 10 mg, per day in the form of injections.

EXAMPLES

The following describes the present invention in detail based on examples, but the present invention is not limited by the examples. In this connection, unless otherwise noted, experiments were carried out in accordance with the conventionally known method (Sambrook, J. et al., "Molecular Cloning—A Laboratory Manual", Cold Spring Harbor Laboratory, NY, 1989) such as gene manipulation experimentation manuals and manuals attached to reagents and the like.

Example 1

Preparation of a Novel Oxidase NOX1-b and Determination of Complete Length Open Reading Frame (ORF)

Using an RNA extraction kit (RNAeasy Protect Mini Kit) manufactured by Qiagen, mRNA was purified from an RA patient-derived synovial cell (HS-RA) manufactured by Toyobo and converted into cDNA using SUPERSCRIPT II (SUPERSCRIPT First-Strand Synthesis System for RT-PCR) (Gibco-BRL), and the thus obtained homemade cDNA was used as the template. Oligo DNA fragments coding for the outside of NOX1 ORF, represented by SEQ ID NO:3 and SEQ ID NO:4, were synthesized, and a PCR reaction of 94° C. for 1 minute and 35 cycles consisting of 94° C. for 30 seconds, 55° C. for 30 seconds and 68° C. for 3 minutes, was carried out using a DNA polymerase (PLATINUM™ Taq DNA polymerase; mfd. by Invitrogen). The cDNA obtained by the reaction was inserted into a cloning vector (TA cloning kit; mfd. by Invitrogen) (NOX1 vector) and analyzed by the dideoxy terminator method using ABI3700 DNA Sequencer (mfd. by Applied Biosystems) to determine the ORF sequence. This gene was named NOX1-b. Complete length nucleotide sequence of the gene is shown in SEQ ID NO:1, and its deduced amino acid sequence in SEQ ID NO:2. The ORF sequence of NOX1-b encoded a novel protein in which from the 433rd position to the 481st position of NOX1 (GenBank accession number: AF127763) are spliced out.

Example 2

Cloning of NOX1-b Complete Length ORF and Construction of Protein Expression Plasmid The NOX1-b vector prepared in Example 1 was digested with EcoRI and XhoI and inserted into the EcoRI and XhoI sites of a protein expression vector (pcDNA3.1/HisB; mfd. by Invitrogen), thereby completing a complete length protein expression plasmid pcDNA3.1/HisB•NOX1-b.

Example 3

Expression of HisB•NOX1-b in Animal Cell Strain

NIH3T3 cells (mfd. by Dainippon Pharmaceutical) were spread on a 10 cm plate at a density of $1 \times 10^6$ cells and cultured for 12 hours, and then the expression plasmid pcDNA3.1/HisB•NOX1-b prepared in Example 2 and the vacant vector pcDNA3.1/HisB were introduced into the NIH3T3 cells using a transfection reagent (FuGENE™ 6 Transfection Reagent; mfd. by Roche) in accordance with the instructions attached thereto. After 12 to 16 hours of the plasmid introduction, the medium was replaced by a serum-free medium and then the culturing was continued for 48 hours to 60 hours. The introduced cells were washed with PBS and then recovered with an SDS sample buffer (S.B). The presence of the subject protein in the S.B was confirmed by a western blotting using an antibody which recognizes a C-terminal sequence common to the NOX1 protein and NOX1-b protein as an epitope (rabbit anti-MOX antibody; mfd. by Santa Cruz). That is, the thus recovered aforementioned S.B was subjected to an SDS/4%–20% acrylamide gel (mfd. by Daiichi Pure Chemicals) electrophoresis (under reduction condition) and then transferred on a PVDF membrane (mfd. by Millipore) using a blotting device. After the transfer, the PVDF membrane was blocked by adding Block Ace (mfd. by Dainippon Pharmaceutical) and then allowed to react with a biotinylated rabbit anti-IgG antibody (M2; mfd. by Sigma) and a horseradish peroxidase-labeled streptavidin (mfd. by Amersham Pharmacia) in that order. After the reaction, expression of the subject protein was verified using an ECL western blotting detection system (mfd. by Amersham Pharmacia). A band of 52±0.5 kD in molecular weight was detected in the sample obtained from the cells introduced with pcDNA3.1/HisB•NOX1-b, but the band was not detected in the sample obtained from the vacant vector-introduced cells, so that it was found that HisB•NOX1-b is expressed in the cells introduced with pcDNA3.1/HisB•NOX1-b.

Example 4

Expression Increase of NOX1-b mRNA in RA Patient-derived Synovial Cells

Using the mRNA extraction method shown in Example 1, a homemade cDNA was prepared from healthy person-derived synovial cells (Cell System-SS cells) manufactured by Dainippon Pharmaceutical. By synthesizing probe primers coding for the NOX1-b-specific sequences represented by SEQ ID NO:5 and SEQ ID NO:6, a semi-quantitative RT-PCT reaction of 94° C. for 1 minute and 45 cycles consisting of 94° C. for 10 seconds, 55° C. for 20 seconds and 72° C. for 30 seconds, was carried out on each of RA patient- and healthy person-derived samples (prepared by diluting each template cDNA at 1, 1/10 and 1/100 times dilution ratios), using a DNA polymerase (r Taq DNA polymerase; mfd. by Toyobo). The primer sequence represented by SEQ ID NO:5 is a nucleotide sequence coding for a connecting region from which NOX1 was spliced out, namely the region where the 432nd position and the 482nd position of the NOX1 protein are connected, so that this is a sequence which does not recognize NOX1. Accordingly, the PCR products by SEQ ID NO:5 and SEQ ID NO:6 are NOX1-b-specific. When the PCR reactants were subjected to an agarose gel electrophoresis and the DNA fragments were detected by ethidium bromide (EtBr) staining, a band having a size considered to be that of NOX1-b was found in the RA patient-derived sample, but was not able to be found in the sample of healthy person. On the other hand, in the control PCR reaction of glyceraldehyde 3-phosphate dehydrogenase (G3PDH) carried out using the primers represented by SEQ ID NO:7 and SEQ ID NO:8, the same band was found by the EtBr staining in both of the RA patient- and healthy person-derived samples (FIG. 1A). Additionally, the RT-PCR reaction was carried out on each of RA patient- and healthy person-derived samples in the same manner as in the above using probe primers coding for conventionally known NOX1-specific sequences represented by SEQ ID NO:13 and SEQ ID NO:6, and the results were compared with the data obtained by the use of the NOX1-b-specific probe primers. As a result, different from the case of NOX1-b, a band having a size considered to be that of NOX1 was found not only in the RA patient-derived samples but also in the healthy person-derived samples. In addition, changes in the band quantity of NOX1 stained by EtBr were not found in the RA patient-derived samples and healthy person-derived samples (FIG. 1B). Based on these results, it was revealed that expression of NOX1-b is significantly accelerated in the RA patient-derived synovial cells in comparison with the case of healthy person. It was also found that inspection of RA diagnosis can be carried out by the method described in this example.

Example 5

ROS Producing Activity of NOX1-b

Figure 2:
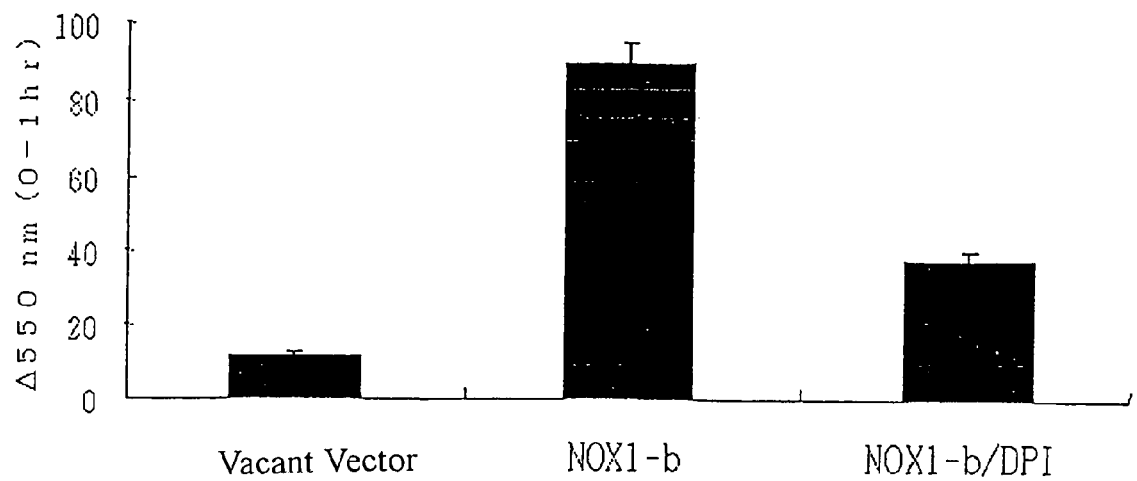
FIG. 2 shows ROS producing activity of NOX1-b and inhibition by DPI.

Using the NOX1-b expressing cells shown in Example 3, the ROS productivity was measured by a cytochrome C reduction method. In order to measure ROS by the cytochrome C reduction method, vacant vector expressing cells and NOX1-b expressing cells were respectively dispensed in $0.5 \times 10^6$ cells/100 μl/well portions into a 96 well multi-well plate for cell culture (to be referred to as multi-well plate). About 12 hours thereafter, 4.62 mg/ml of cytochrome C was added and mixed in 100 μl/well portions under respective conditions, and then the multi-well plate was set on a plate reader to periodically measurement of absorbance at 550 nm. Integrated values after 1 hour thereof are shown in FIG. 2. As a result, it was revealed that the NOX1-b expressing cells have significant ROS producing activity in comparison with the vacant vector expressing cells. Additionally, it was found that the activity is considerably inhibited when 1 μM of diphenylene iodonium chloride (to be referred to as DPI) known as an NADPH oxidase inhibitor is added 30 minutes before the addition of cytochrome C (FIG. 2). Based on these results, it was revealed that NOX1-b has ROS producing activity, and the activity is inhibited by DPI. A substance capable of inhibiting the activity of NOX1-b can be screened by the measuring method of the example.

Example 6

Upregulation of COX-2 mRNA in NOX1-b Expressing Cells

Figure 3:
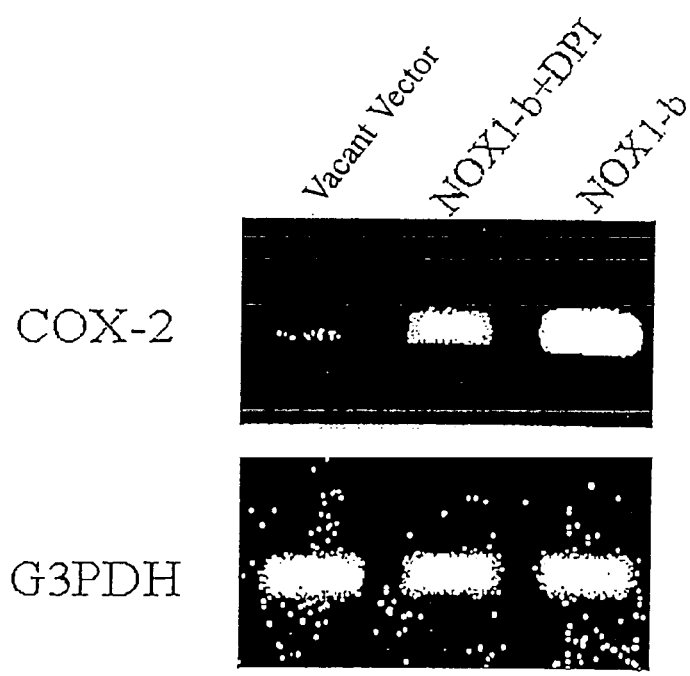
FIG. 3 shows increase in the expression of COX-2 mRNA and inhibition by DPI in NOX1-b expressing cells.

Using the mRNA extraction method shown in Example 1, respective cDNA samples were prepared from the vacant vector expressing cells and NOX1-b expressing cells. By synthesizing probe primers coding for the COX-2-specific sequences represented by SEQ ID NO:9 and SEQ ID NO:10, an RT-PCT reaction of 94° C. for 1 minute and 45 cycles consisting of 94° C. for 10 seconds, 55° C. for 20 seconds and 72° C. for 30 seconds, was carried out on each of the vacant vector expressing cell- and NOX1-b expressing cells-derived samples using a DNA polymerase (r Taq DNA polymerase; mfd. by Toyobo). When the PCR reactants were subjected to an agarose gel electrophoresis and the DNA fragments were detected by EtBr staining, it was confirmed that a band having a size considered to be that of COX-2 is considerably increased in the NOX1-b-derived samples in comparison with the case of vacant vector-derived samples (FIG. 3). On the other hand, in the control PCR reaction of G3PDH carried out using the primers represented by SEQ ID NO:7 and SEQ ID NO:8, the same band was found by the EtBr staining in both of the vacant vector expressing cell- and NOX1-b expressing cell-derived samples (FIG. 3). Accordingly, it was revealed that expression of COX-2 is significantly accelerated in the NOX1-b expressing cells in comparison with the vacant vector expressing cells.

When DPI which is the NOX1-b inhibitor was added to the NOX1-b expressing cells to a final concentration of 1 μM and RT-PCR similar to the above was carried out 3 hours thereafter using the sample which was prepared by mRNA extraction method, it was revealed that induction of COX-2 expression by NOX1-b expression is inhibited by DPI (FIG. 3). Since the induction of COX-2 expression was inhibited by DPI, it was considered that expression of COX-2 was induced via the oxidation-reduction control by an NOX1-b-derived ROS.

Example 7

Expression Increase of TNFα mRNA in NOX1-b Expressing Cells

Figure 4:
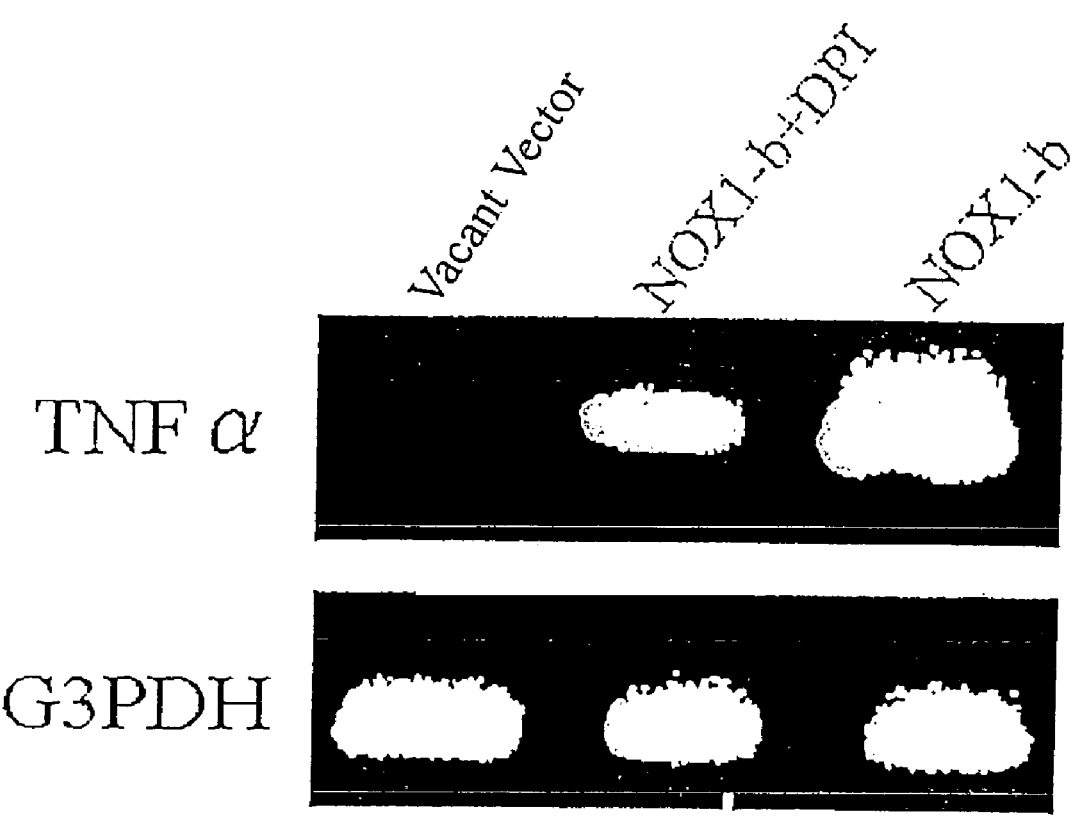
FIG. 4 shows increase in the expression of TNF-α mRNA and inhibition by DPI in NOX1-b expressing cells.

Probe primers coding for the TNF-α-specific sequences represented by SEQ ID NO:11 and SEQ ID NO:12 were synthesized. On each of the cDNA samples prepared in Example 6 and using a DNA polymerase (r Taq DNA polymerase; mfd. by Toyobo), RT-PCR reaction of 94° C. for 1 minute, 45 cycles of consisting of 94° C. for 10 seconds and 55° C. for 20 seconds and 72° C. for 30 seconds, was carried out. When the PCR reactants were subjected to an agarose gel electrophoresis and the DNA fragments were detected by ethidium bromide (EtBr) staining, a band having a size considered to be that of TNF-α was found in the NOX-1b expressing cell-derived sample, but was not able to be found in the vacant vector expressing cell-derived sample. On the other hand, in the control PCR reaction of G3PDH carried out using the primers represented by SEQ ID NO:7 and SEQ ID NO:8, the same band was found by the EtBr staining in both of the vacant vector expressing cell- and NOX1-b expressing cell-derived samples. Additionally, it was revealed that the induction of TNF-α expression is inhibited when the NOX1-b-derived cells are pretreated for 3 hours with 1 μM of DPI which is the NOX1-b inhibitor (FIG. 4). Accordingly, it was revealed that expression of TNF-α is significantly accelerated in the NOX1-b expressing cells in comparison with the case of vacant vector expressing cells. In addition, since the induction of TNF-α expression is inhibited by DPI, it is considered that the induction is carried out via the oxidation-reduction control by an NOX1-b-derived ROS.

INDUSTRIAL APPLICABILITY

It was revealed that the polynucleotide of the present invention can be used as an index of RA diagnosis, because its expression acceleration reflects the pathology. It became possible to carry out inspection of the RA diagnosis, by using the expression of the polynucleotide of the present invention and of the polypeptide of the present invention encoded by the polynucleotide as indexes. Additionally, the present invention provides a novel oxidase which is expressed specifically in RA patient-derived synovial cells, and it is expected that PCR using the specific primer sequences can be applied to the inspection of diagnosis of RA. The screening method of the present invention is useful for the screening of a substance for the treatment of RA and/or a substance for the treatment of osteoarthritis.

Thus, although the present invention has been described in the foregoing based on specified embodiments, its modifications and improvements obvious to those skilled in the art are included in the scope of the present invention.

The invention claimed is:

1. An isolated polypeptide consisting of the amino acid sequence of SEQ ID NO:2.

2. A screening method, comprising:
   (1) contacting a test substance with a cell expressing a recombinant polypeptide, said polypeptide consisting of the amino acid sequence of SEQ ID NO:2, wherein said polypeptide produces $O_2^-$, increases expression of Tumor Necrosis Factor-α (TNF-α), and/or increases expression of cyclooxygenase-2 (COX-2);
   (2) determining whether said test substance inhibits at least one of: (i) said production of $O_2^-$, (ii) said increase in expression of TNF-α, and (iii) said increase in expression of COX-2; and
   (3) selecting a substance capable of inhibiting at least one of: (i) said production of $O_2^-$, (ii) said increase in expression of TNF-α, and (iii) said increase in expression of COX-2.

* * * * *